United States Patent [19]

Ghyczy et al.

[11] Patent Number: 4,681,617

[45] Date of Patent: Jul. 21, 1987

[54] PHOSPHOLIPID COMPOSITIONS AND THEIR USE IN PLANT PROTECTION SPRAY MIXTURES

[75] Inventors: Miklos Ghyczy, Cologne; Paul-Robert Imberge, Pulheim; Armin Wendel, Cologne, all of Fed. Rep. of Germany

[73] Assignee: A. Nattermann & Cie, GmbH, Cologne, Fed. Rep. of Germany

[21] Appl. No.: 755,967

[22] Filed: Jul. 17, 1985

Related U.S. Application Data

[63] Continuation-in-part of Ser. No. 508,662, Jun. 28, 1983, abandoned.

[30] Foreign Application Priority Data

Jul. 9, 1982 [DE] Fed. Rep. of Germany ....... 3225703

[51] Int. Cl.$^4$ ..................... A01N 57/00; B01F 17/34; B01J 13/00
[52] U.S. Cl. ................. 71/86; 47/DIG. 11; 71/DIG. 1; 252/312; 252/356; 514/937; 514/941
[58] Field of Search ............... 252/312, 356; 260/403; 71/DIG. 1, 86; 514/937, 941; 47/DIG. 11

[56] References Cited

U.S. PATENT DOCUMENTS

| | | | |
|---|---|---|---|
| 2,296,933 | 9/1942 | Jordan | 252/356 X |
| 2,849,318 | 8/1958 | Julian et al. | 260/403 X |
| 3,069,361 | 12/1962 | Cogswell | 252/356 X |
| 3,900,421 | 8/1975 | Fusey | 252/312 |
| 4,200,551 | 4/1980 | Orthoefer | 252/356 X |
| 4,252,793 | 2/1981 | Altman | 252/356 X |

FOREIGN PATENT DOCUMENTS 0068295 1/1983 European Pat. Off. .
0082437 6/1983 European Pat. Off. .

*Primary Examiner*—Richard D. Lovering
*Attorney, Agent, or Firm*—Herbert B. Keil

[57] ABSTRACT

Phospholipid concentrates from natural or synthetic phospholipids and physiologically acceptable organic solvents and further additives of the following composition:

20–60 wght. % phospholipids
0–23 wght. % glycerin
5–62.5 wght. % organic solvent
0–30 wght. % co-emulsifier
0–35 wght. % dissolving intermediary
0–15 wght. % water
0–15 wght. % vegetable oil or neutral oil The phospholipids are a mixture of phosphatidyl choline, phosphatidyl ethanol amine, N-acetyl phosphatidyl ethanol amine, and other phosphatides, the concentrates perferably containing a mixture of 10–50 wght. % phosphatidyl choline, 10–30 wght. % phosphatidyl diethanol amine, 10–30 wght. % N-acylphosphatidyl ethanol amine, and 3–10 wght. % other phosphatides, in relation to the total quantity of phospholipids. The phospholipid concentrates are particularly suitable as auxiliary agents in the production and application of spray mixtures containing plant protectants.

8 Claims, No Drawings

PHOSPHOLIPID COMPOSITIONS AND THEIR USE IN PLANT PROTECTION SPRAY MIXTURES

This application is a continuation-in-part of application Ser. No. 508,662, filed on June 18, 1983 and now abandoned.

The object of the invention is a phospholipid concentrate suitable for use as an auxiliary agent in the production and application of plant protectant spray mixture.

Phospholipids, natural or synthetic, are known, and consist of component parts of commercially available lecithins. Phospholipids are generally plastic, difficult to work with masses which are soluble in organic solvents, e.g. hexane or mineral oil. Chemically they include phosphatidyl choline, hydrogenated phosphatidyl cholines, phosphatidyl inositol, phosphatidyl serine, phosphatidic acid, phosphatidyl glycerol, or a mixture of several such products, e.g. mixtures of phosphatidyl choline and phosphatidyl ethanol amine or phosphatidyl choline with phosphatidyl ethanol amine and N-acyl phosphatidyl ethanol amine, or other phosphatidyl choline mixtures. Natural phosphatidyl cholines can be obtained from the processes described in the following patents: DE-PS 10 47 597, DE-PS 10 53 299, DE-PS 16 17 679, DE-PS 16 17 680, the German patent applicatins DE-OS 30 47 048, DE-OS 30 47 012, or DE-OS 30 47 011.

The Japanese patent publication J 5 6070-826 describes an oil in polyvalent alcohol emulsion compound which contains lecithin, a polyvalent alcohol, and a non-ionogenic surface-specific agent. Involved are transparent or opaque gels or highly viscous liquids, which can be employed for various purposes. O/W emulsions arise upon stirring in water. It has been shown that these gels, together with plant protectants, cannot without difficulty be diluted to form spray mixtures.

For certain purposes of application, liquid phospholipid concentrate preparations which can be easily and simply introduced into aqueous systems, for example plant protectant spray mixtures, are desirable.

The objective of the invention is to create a phospholipid concentrate whose composition allows it to be simply mixed into aqueous systems and which is compatible with the active ingredients contained in that system.

This objective is achieved by the phospholipid concentrates described in the patent claims, which are suitable for use as an auxiliary agent.

The invention also includes the application of the phospholipid concentrates as auxiliary agents in the production and application of spray mixtures containing plant protectants.

The invention phospholipid concentrates from natural or synthetic phospholipids and physiologically acceptable organic solvents and further additives consist of (a) 5–60 wght.% natural or synthetic phospholipid from the group of phosphatidyl choline, hydrogenated phosphatidyl choline, phosphatidyl ethanol amine, N-acyl phosphatidyl ethanol amine, phosphatidyl ethanol amine, phosphatidyl inositol, phosphatidyl serine, and phosphatidyl glycerol, and the mixture of such products;

(b) 5–62.5 wght.% physiologically acceptable solvent from the group of alcohols, ethers or ketone(3,5,5-trimethyl-2-cyclohexene-1 on), dimethyl sulfoxide, or a mixture of such solvents;

(c) up to 30 wght.% non-ionogenic co-emulsifier;

(d) up to 35 wght.% dissolving intermediary from the group of sorbitan fatty acid esters, triglyceride or partial glyceride mixtures of saturated fatty acids, and the hydroxy ethyl amides; if need be (e) up to 23 wght.% glycerin and, if need be (f) up to 15 wght.% water and/or up to 25 wght.% vegetable oil or neutral oil.

The phospholipid concentrates will best contain 20–60 wght.% phospholipids in keeping with (a) above.

Particularly preferred are phospholipid mixtures of phosphatidyl choline, phosphatidyl ethanol amine, N-acyl phosphatidyl ethanol amine, and other phosphatides. A mixture of this type consists of 10–50 wght.% phosphatidyl choline, 10–30 wght.% phosphatidyl ethanol amine, 10–30 wght.% N-acyl phosphatidyl ethanol amine, and 3–10 wght.% other phosphatides, in relation to the total quantity of the phospholipid mixture.

Of the N-acyl phosphatidyl ethanol amines, those particularly are recommended in which the acyl group is derived from saturated or olefinically unsaturated fatty acids with 2 to 20 carbon atoms, preferably saturated acids with 2–5 C atoms or the saturated or olefinically unsaturated ones with 14, 16, 18, or 20 C atoms.

To obtain a liquid preparation, a physiologically acceptable organic solvent or solvent mixture is employed. The employed solvent can be alcohol or ether, for example, methanol, ethanol, propanol, isopropanol, butanol, isobutanol, tert. butanol, sec. butanol, ethylene glycol, ethylene glycol monoethyl ether, ethylene glycol monomethyl ether, ethylene glycol dimethyl ether, ethylene glycol diethyl ether, diethylene glycol dimethyl ether, diethylene glycol monoethyl ether, diethylene glycol monomethyl ether, diethylene glycol propyl ether, diethylene glycol diethyl ether, polyethylene glycol, polypropylene glycols, polypropylene glycol monomethyl ether, polypropylene glycol monoethyl ether, propylene glycol methyl ethyl, polypropylene diethyl ether, butylene glycol, tetrahydrofurane, dioxane, dimethyl sulfoxide, 3,5,5-trimethyl-2-cyclohexene-1-on. Preferred solvents are the last mentioned, $C_1$–$C_4$ alkyl alcohols, dimethyl sulfoxide, ethylene glycol monoethyl ether, or mixtures of the same. Particularly suitable as nonionogenic co-emulsifiers are the ethoxylates of fatty alcohols or hydrogenated castor oil or nonyl phenol or fatty acide amides. Other non-ionogenic emulsifiers can also be used, however.

The employed dissolving intermediaries can be sorbitan fatty acid ester, triglyceride or partial glcyeride mixtures of saturated fatty acids, hydroxy ethylamides, such as N-(2-hydroxy ethyl)caproic acid amide, N-(2-hydroxy ethyl) valeric acid amide, or N-(2-hydroxyethyl)heptane acid amide.

Along with these components, which are essential to the mixing behavior of the aqueous systems, the invention concentrates can also contain portions of water and/or vegetable oils or neutral oils, as well as glycerin, which facilitates mixture in the aqueous systems.

The invention phospholipid concentrates are produced by mixing the solvent, glycerin, the co-emulsifiers, and the dissolving intermediaries, at room temperature or at a slightly increased temperature. The phospholipid is then added and stirred at about 20° C. until a homogeneous preparation is formed. Water and vegetable oils are finally added under slow stirring and worked into the concentrate.

The composition of the invention phospholipid concentrates will be further elucidated by means of the following example.

EXAMPLE 1

Composition of phospholipid concentrate:
 40 wght.% phospholipids
 35 wght.% 3,5,5-trimethyl-2-cyclohexene-1-on (isophorone)
 15 wght.% glycerin
 5 wght.% nonylphenolethoxylate
 5 wght.% N-(2-hydroxyethyl)-caprionic acid amide Isophorone, glycerin, nonylphenolethoxylate and N-(2-hydroxyethyl)-caprionic acid amide are first mixed together; the phospholipid mixture is then added under stirring; stirring continues until a homogeneous preparation is formed.

EXAMPLE 2

Composition of phospholipid concentrate:

| wght. % | | |
|---|---|---|
| 26.6 wght. % | phospholipid mixture of: | |
| | phosphatidylcholine | 42% |
| | phosphatidylethanolamine | 25% |
| | N—acylphosphatidylethanolamine | 25% |
| | other phosphatides | 8% |
| 10 wght. % | glycerin | |
| 23.4 wght % | isophorone | |
| 3.3 wght % | castor oil, ethoxylated | |
| 3.3 wght % | sorbitan monopalmitate | |
| 13.4 wght % | water | |
| 20 wght % | vegetable oil or neutral oil | |

EXAMPLE 3

Composition of phospholipid concentrate:

| | | |
|---|---|---|
| 40 wght. % | phospholipid mixture of: | |
| | phosphatidylcholine | 45% |
| | phosphatidylethanolamine | 25% |
| | N—acylphosphatidylethanolamine | 21% |
| | other phosphatides | 9% |
| 5 wght. % | isophorone | |
| 15 wght. % | glycerin | |
| 30 wght. % | nonylphenolethoxylate | |
| 10 wght. % | sorbitan monolaurate | |

EXAMPLE 4

Composition of phospholipid concentrate:

| | | |
|---|---|---|
| 32 wght. % | phospholipid mixture of: | |
| | phosphatidylcholine | 40% |
| | phosphatidylethanolamine | 28% |
| | N—acylphosphatidylethanolamine | 27% |
| | other phosphatides | 5% |
| 15 wght. % | glycerin | |
| 35 wght. % | isophorone | |
| 5 wght. % | polyoxyethyleneglycol monooleate | |
| 5 wght. % | sorbitan monooleate | |
| 8 wght. % | ethanol | |

EXAMPLE 5

Composition of phospholipid concentrate:

| wght. % | | wght. pts. |
|---|---|---|
| 20 | phospholipid mixture of | |
| | phosphatidyl choline | 42 |
| | phosphatidyl ethanol amine | 25 |
| | N—acyl phosphatidyl ethanol amine | 25 |
| | phosphatidyl glycerol | 8 |
| 45 | solvent, dioxane | |
| 30 | co-emulsifier, ethoxylated castor oil | |
| 5 | dissolving intermediary, sorbitane mono palmitate. | |

The co-emulsifier and the solvent and the dissolving intermediary are first mixed together. The phospholipid mixture is then added under stirring, stirring is continued until a homogeneous preparation is formed.

EXAMPLE 6

Composition of the phospholipid concentrate:

| wght. % | | wght. pts. |
|---|---|---|
| 26.5 | phospholipid mixture of | |
| | phosphatidyl choline | 40 |
| | phosphatidyl ethanol amine | 28 |
| | N—acyl phosphatidyl ethanol amine | 27 |
| | phosphatidyl serine and phosphatidic acid | 5 |
| 35.2 | solvent, 3,5,5-trimethyl-2-cyclohexene-1-on (isophorone) | |
| 3.3 | co-emulsifier, nonyl-phenol-ethoxylate | |
| 35 | dissolving intermediary sorbitane monopalmitate. | |

Solvent co-emulsifier and dissolving intermediary are first mixed together and stirring is continued. The phospholipid mixture is then added under stirring, stirring continues until a homogeneous preparation is formed.

EXAMPLE 7

Composition of the phospholipid concentrate:

| wght. % | | wght. pts. |
|---|---|---|
| 40 | phospholipid mixture of | |
| | phosphatidyl choline | 45 |
| | phosphatidyl ethanol amine | 25 |
| | N—acyl phosphatidyl ethanol amine | 21 |
| | phosphatidyl glycerol and phosphatidyl serine | 9 |
| 5 | solvent, 3,5,5-trimethyl-2-cyclohexene-1-on | |
| 15 | glycerin | |
| 30 | co-emulsifier, nonyl-phenol-ethoxylate | |
| 10 | solving intermediary sorbitane monolaurute. | |

EXAMPLE 8

Composition of the phospholipid concentrate:

| wght. % | | wght. pts. |
|---|---|---|
| 32 | phospholipid mixture of | |
| | phosphatidyl choline | 40 |
| | phosphatidyl ethanol amine | 28 |
| | N—acyl phosphatidyl ethanol amine | 27 |
| | phosphatidyl glycerol and phosphatidyl serine | 5 |
| 15 | glycerin | |
| 35 | solvent, 3,5,5-trimethyl-2-cyclohexene-1-on | |
| 8 | solvent, ethanol | |

-continued

| wght. % | | wght. pts. |
|---|---|---|
| 5 | co-emulsifier, polyoxy-ethelene-glykol mono-oleate | |
| 5 | dissolving intermediary sorbitane-mono oleate. | |

EXAMPLE 9

Composition of the phospholipid concentrate:

| wght. % | | wght. pts. |
|---|---|---|
| 40 | phospholipid mixture of | |
| | phosphatidyl choline | 40 |
| | phosphatidyl ethanol amine | 30 |
| | N—acyl phosphatidyl ethanol amine | 25 |
| | mixture of phosphatidyl serine, phosphatidyl glycerol and phosphatidyl inosite | 5 |
| 35 | solvent, 3,5,5-trimethyl-2-cyclohexene-1-on | |
| 15 | glycerin | |
| 5 | co-emulsifier, nonyl-phenol-ethoxylate | |
| 5 | dissolving intermediary, N—(2-hydroxy ethyl)-caproic acid amide. | |

Solvent, glycerine, nonyl phenol ethoxylate and the caproic acid amide are first mixed together. The phospholipid mixture is then added under stirring, stirring cotinues until a homogeneous preparation is formed.

EXAMPLE 10

Composition of the phospholipid concentrate:

| wght. % | |
|---|---|
| 25 | phospholipid mixture of example 5 |
| 40 | solvent, 3,5,5-trimethyl-2-cyclohexene-1-on |
| 22.5 | glycerin |
| 7.5 | co-emulsifier, nonyl-phenol-ethoxylate |
| 5 | dissolving intermediary, sorbitane-mono-oleate |

EXAMPLE 11

Composition of the phospholipid concentrate:

| wght. % | | wght. pts. |
|---|---|---|
| 26.6 | phospholipid mixture of | |
| | phosphatidyl choline | 42 |
| | phosphatidyl ethanol amine | 25 |
| | N—acyl phosphatidyl ethanol amine | 25 |
| | phosphatidyl glycerol and phosphatidyl serine | 8 |
| 10 | glycerin | |
| 36.8 | solvent, 3,5,5-trimethyl-2-cyclohexene-1-on | |
| 3.3 | co-emulsifier, castor oil ethoxylated | |
| 3.3 | dissolving intermediary, sorbitane-mono-palmitate | |
| 20 | vegetable oil or neutral oil. | |

EXAMPLE 12

Composition of the phospholipid concentrate:

| weight. % | |
|---|---|
| 35 | phospholipid mixture of example 7 |
| 5 | solvent, methanol |
| 25 | dissolving intermediary, sorbitane-mono-laurate |

| weight. % | |
|---|---|
| 25 | neutral oil |
| 10 | co-emulsifier, castor oil ethoxylated. |

The phospholipid concentrates under the invention are particularly suited to serve as auxiliary agents in the production and application of spray mixtures containing plant protectants.

Due to their easy handling with respect to transport, storage, and application, plant protectants active against parasites and weeds are commercially available today as active ingredient concentrates in the form of emulsions (EC), suspensions (SC), solutions (LC) or easily wetted powders (BP), and are usually applied in liquid form, e.g. as solutions, suspensions, or emulsions. Before being sprayed the concentrates are diluted or moistened with the quantity of water indicated by the manufacturer and are then sprayed in the form of spray mixture on land or by air with conventional equipment.

A disadvantage of most spray mixtures is that the known spraying devices produce such small droplets that the resulting spray mist is driven off course, particularly due to the effect of wind, and the agricultural area to be treated is not adequately covered, while additional areas are sprayed.

Also of significance is the direct drift of the sprayed plant protectants, which partially vaporize due to their volatility and are driven onto neighboring areas due to the air mass exchange with the wind. Depending on the volatility of the preparations, correspondingly high doses are required in order to assure than adequates quantities of the active ingredient reach the intended areas.

Both forms of drift represent an unnecessary environmental load, and damage to vegetation and fauna on areas not intended for spraying is frequently caused by the active substances, with the result that necessary spraying cannot be performed at the correct time if climatic conditions are unfavorable.

Application is facilitated considerably if the invention phospholipid concentrates are used as additional auxiliary agents in preparing the plant protectant spray mixtures, and stable droplets will be created with a small portion of droplets whose size is less than 200 micrometers, thus considerably reducing drift. Furthermore, the addition of phospholipid concentrates considerably facilitates the production of the spray mixtures.

In the process conventional active ingredient concentrates are first diluted with water; a phospholipid concentrate is then added to the mixture. It is also possible, however, to separately dilute the commercially available active ingredient concentrates and the phospholipid concentrates with water to form spray mixtures, and to then mix the two diluted mixtures before spraying. In the case of liquid active ingredient concentrates it is also possible to first mix the conventional active ingredient concentrate with the invention phospholipid concentrate and to then dilute the mixture with water to form a spary mixture.

The phospholipid concentrate is used in a quantity such that the ratio by weight of the active ingredient to the phospholipid is from 1:0.5 to 1:5, preferably from 1:1 to 1:2.

The active ingredients are plant protectants in the usual solution, emulsion, or suspension concentrates or in the form of wettable powders, containing herbicidal, fungicidal, insecticidal, acaricidal, or nematocidal agents.

COMPARATIVE EXPERIMENT

1. Mixture from the Japanese Patent Disclosure J 5 6070-826:
   0.3 g lecithin
   0.2 g sorbitol monooleate
   5.0 g olive oil
   2.5 g glycerin
   2.5 g sorbitol
are mixed to form a transparent gel.
2. Mixture with composition invention example 4:
   Method of procedure:
   1. Commercial plant protectant is dissolved in water and phospholipid mixture is added.
   2. Phospholipid mixture is added to water, the commercial plant protectant is mixed in.
   3. Commercial plant protectant and phospholipid mixture are jointly stirred into water.
   4. Commercial plant protectant and phospholipid mixture are separately stirred into water and then combined.

Under methods of procedure 1–4 spray mixtures of 100 ml each were produced, containing 0.1 g triadimefon as active ingredient and 0.5 g of the phospholipid mixture under the Japanese patent application or the invention.

Stable, homogeneous spray mixtures were obtained with the invention phospholipid mixture employing all four methods.

With the state-of-the-art phospholipid mixture methods 2 and 4 could not be performed, since the gel could not be stirred with water. It was not possible to create homogeneous spray mixtures according to methods 1 and 3; these methods could not, therefore, be applied.

The invention phospholipid concentrate has been proven to be particularly effective with the following active ingredients:

| active ingredient | form of concentrate | active ingredient concentration in spray mixture, in mg/l |
|---|---|---|
| fungicides | | |
| triadimefon | spray powder | 250 |
| copper oxychloride | wettable powder | 1350 |
| propineb | wettable powder | 1400 |
| procymidone | wettable powder | 375 |
| wettable sulfur | wettable powder | 2000 |
| herbicides | | |
| glyphosat | aqueous solution | 4800 |
| linuron | spray powder | 1763 |
| terbuthylazine | suspension | 10,000 |
| flampropisopropyl | emulsion | 1750 |
| trifluralin | emulsion | 3216 |
| dinoseb acetate | emulsion | 4920 |
| chlormequatchloride | aqueous solution | 7800 |
| chloridazone | suspension | 6450 |
| isoproturon | wettable powder | 5025 |
| alloxydim-Na | soluble powder | 6563 |
| atrazin | wettable powder | 3600 |
| insecticides | | |
| malathion | emulsion | 20,400 |
| propoxur | emulsion | 400 |
| permethrin | emulsion | 225 |
| cypermethrin | emulsion | 240 |
| heptenophos | emulsion | 1000 |

The chemical names are given below for the plant protectants, identified above by their international brief designations.

| brief designation | chemical name |
|---|---|
| triadimefon | 1-(4-chlorophenoxy)-3,3-dimethyl-1-(1,2,4-triazole-1-yl)-butanone |
| propineb | zinc-propylenebis(dithiocarbamate) |
| procymidone | N—(3,5-dichlorophenyl)-1,2-dimethyl-cylcopropane-1,2-dicarboximide |
| glyphosat | N—phosphone-methylglycine |
| linuron | N—(3,4-dichlorphenyl)-N'—methoxy-N'—methyl urea |
| terbuthylazin | 2-chloro-4-tert.butyl-amino-6-ethylamino-1,3,5-triazine |
| flampropisopropyl | 2-(N—benzyo-3-chloro-4-fluorophenylamino)-propionic acid-isopropylester |
| trifluralin | 2,6-dinitro-N,N—dipropyl-4-trifluoromethyl-aniline |
| dinoseb-acetate | 2-sec.butyl-4,6-dinitrophenyl-acetate |
| chlormequat-chloride | 2-chloroethyl trimethyl ammonium chloride |
| chloridazone | 5-amino-4-chloro-2-phenylpyridazine-3-on |
| isoproturon | 3-(4-isopropylphenyl)-1,1-dimethyl urea |
| alloxydim-Na | 2,1-(N—alloxyaminobutylidene-4-methoxy-carbonyl)-5,5-dimethylcyclohexane-1,3-diene-sodium salt |
| atrazin | 2-chloro-4-ethylamino-6-isopropylamino-1,3,5-triazine |
| malathion | S—1,2-bis(ethoxycarbonyl)ethyl-0,0-dimethyl-phosphorodithioate |
| propoxur | 2-isopropoxyphenylmethylcarbamate |
| permethrin | 3-phenoxyphenylmethyl-3-(2,2-dichloro-ethenyl)-2,2-dimethylcyclopropane-carboxylate |
| cypermethrin | N—cyano-3-phenoxybenzyl-3-(2,2-dichloroethenyl)-2,2-dimethylcyclo-propane-carboxylate |
| heptenophos | 7-chlorobicyclo/3,2,0/-hepta-2,6-diene-6-yl-dimethylphosphate |

We claim:

1. A phospholipid concentrate suitable as an auxiliary agent in the production and application of plant protectant spray mixtures comprising
   (a) 5 to 60 weight percent natural or synthetic phospholipid from the group consisting of phosphatidyl choline, hydrogenated phosphatidyl choline, phosphatidyl ethanol amine, N-acyl phosphatidyl ethanol amine, phosphatidyl inositol, phosphatidyl serine, phosphatidyl glycerin, phosphatidic acid and mixtures thereof:
   (b) 5 to 62.5 weight percent physiologically acceptable solvent from the group consisting of an alcohol, an ether, a ketone, dimethyl sulfoxide and mixtures thereof;
   (c) 3.3 to 30 weight percent non-iogenic co-emulsifier comprising ethoxylates of fatty alcohols or hydrogenated castor oil or nonyl phenol or fatty acid amides; and
   (d) 3.3 to 35 weight percent dissolving intermediaries from the group consisting of sorbitan fatty acid esters, the triglyceride or partial glyceride mixtures of saturated fatty acids and the hydroxy ethyl amides.

2. The phospholipid concentrate according to claim 1, wherein the phospholipid concentrate contains a mixture of:
   10–50 weight % phosphatidyl choline;
   10–30 weight % phosphatidyl ethanol amine;
   10–30 weight % N-acylphosphatidyl ethanol amine; and
   3–10 weight % other phosphatides from group (a), in relation to the total quantity of phospholipids.

3. The phospholipid concentrate according to claim 1, wherein the solvent is 3,5,5-trimethyl-2-cyclohexene- 1-on, a $C_1$–$C_4$-alkyl alcohol, dimethyl sulfoxide, ethylene glycol ethyl ether, or mixtures thereof.

4. Phospholipid concentrate according to claim 1 further containing 10 to 23 weight percent glycerine.

5. Phospholipid concentrate according to claim 1 containing also 20 to 25% vegetable oil or neutral oil or a mixture thereof.

6. The phospholipid concentrate according to claim 1 further containing up to 15% water.

7. A spray mixture containing water, a plant protectant and a phospholipid concentrate according to claim 1 wherein the ratio by weight of plant protectant to phospholipid concentrate is from 1:0.5 to 1:5.

8. The spray mixture according to claim 7 wherein said ratio by weight is from 1:1 to 1:2.

* * * * *

UNITED STATES PATENT AND TRADEMARK OFFICE
CERTIFICATE OF CORRECTION

PATENT NO. : 4,681,617
DATED : July 21, 1987
INVENTOR(S) : GHYCZY et al.

It is certified that error appears in the above-identified patent and that said Letters Patent is hereby corrected as shown below:

Title page:

In the abstract:

Line 11, " 0-[15] wght. % vegetable oil or neutral oil "

should be:

-- 0 - 25 wght. % vegetable oil or neutral oil --

Signed and Sealed this

Nineteenth Day of April, 1988

Attest:

DONALD J. QUIGG

Attesting Officer

Commissioner of Patents and Trademarks